United States Patent [19]

Oriel et al.

[11] Patent Number: 4,894,337
[45] Date of Patent: Jan. 16, 1990

[54] PROCESS FOR THE BIOPRODUCTION OF CYCLIC HYDROXIDES

[75] Inventors: Patrick J. Oriel, Midland; Gopalakrishnan Gurujeyalakshmi, East Lansing, both of Mich.

[73] Assignee: Board of Trustees operating Michigan State University, East Lansing, Mich.

[21] Appl. No.: 297,041

[22] Filed: Jan. 17, 1989

[51] Int. Cl.$^4$ ............... C12P 7/22; C12P 7/02/1/04; C12R 1/07
[52] U.S. Cl. .................... 435/156; 435/155; 435/170; 435/832; 435/839
[58] Field of Search ............... 435/155, 156, 170, 832, 435/839, 838

[56] References Cited

U.S. PATENT DOCUMENTS

| | | |
|---|---|---|
| 3,700,560 | 10/1972 | Oppermann. |
| 4,508,822 | 4/1985 | Taylor. |
| 4,705,750 | 11/1987 | Masakazu et al. ............... 435/68 |

FOREIGN PATENT DOCUMENTS

| | | | |
|---|---|---|---|
| 0252567 | 1/1988 | European Pat. Off. ............ | 435/155 |
| 0170800 | 10/1983 | Japan ................................. | 435/832 |
| 0213798 | 12/1983 | Japan ................................. | 435/838 |
| 0045877 | 3/1984 | Japan ................................. | 435/832 |
| 0045878 | 3/1984 | Japan ................................. | 435/832 |
| 00034183 | 2/1985 | Japan ................................. | 435/838 |
| 1012286 | 1/1986 | Japan ................................. | 435/838 |
| 8404541 | 11/1984 | PCT Int'l Appl. ................. | 435/838 |
| 2184126 | 6/1987 | United Kingdom ................ | 435/838 |

OTHER PUBLICATIONS

Freifelder, Microbial Genetics, Jones & Bartlett Publ, 1987, p. 286.
Neujahr, H. Y., and A. Gaal, Eur. J. Biochem. 35:386–400 (1973).
Buswell, J. A., and D. G. Twomey, J. Gen. Microbiol. 87:377–379 (1975).
Buswell, J. A., Biochem. and Biophysical Res. Comm. 70:934–941 (1974).
Buswell, J. A., J. Bacteriol. 124:1077–1083 (1975).
Martin, R. W., Anal. Biochem. 21:1419–1420 (1949).
Irie, S., K. Shirai, S. Doi and T. Yorifuji, Agric. Biol. Chem. 51:1489–1493 (1987).

*Primary Examiner*—Herbert J. Lilling
*Assistant Examiner*—Stephanie Zitomer
*Attorney, Agent, or Firm*—Ian C. McLeod

[57] ABSTRACT

A process for producing useful quantities of a cyclic hydroxide, such as pyrocatechol from a compound having a benzene ring, such as phenol using a Bacillus is described. The process uses tetracycline to inhibit the modification of the cyclic hydroxide by the Bacillus. Pyrocatechol and other related compounds are commercially useful chemicals.

18 Claims, 4 Drawing Sheets

PROCESS FOR THE BIOPRODUCTION OF CYCLIC HYDROXIDES

BACKGROUND OF THE INVENTION

(1) Summary of the Invention

The present invention relates to a process and bacterial cultures which are used to produce useful cyclic hydroxides, preferably aromatic monohydroxides or dihydroxides, from a compound having a benzene ring while inhibiting further degradation of the cyclic hydroxide. In particular, the present invention relates to a process using a phenol resistant Bacillus in a growth medium with an effective amount of tetracycline which inhibits the degradation of pyrocatechol as it is produced.

(2) Prior Art

Phenols present in the effluents of oil refineries, petrochemical plants and other industrial processes are hazardous pollutants and a continuing waste treatment concern. A number of mesophilic microorganisms have been reported to degrade phenol, including *Pseudomonas, Alcaligenes, Streptomyces setonii*, and the yeasts, such as *Trichosporon cutaneum* and *Candida tropicalis* (Neujahr, H. Y., and A. Gaal, Eur. J. Biochem. 35:386–400 (1973). In all cases, phenol proved growth inhibitory even at a modest concentration. It is likely that at least part of this growth inhibition is due to inhibition of phenol hydroxylase, which catalyses the first phenol degradation step. Although this enzyme has proven difficult to solubilize and characterize, inhibition of phenol hydroxylase activity in whole Pseudomonas cells at levels of 0.25 mM phenol is known. With *T. cutaneum*, where solubilization and purification of an NADPH-dependent phenol hydroxylase has been achieved, similar phenol substrate inhibition was observed and attributed to phenol interaction at sites other than the active site. Thus, although oxidation of phenol has been documented for many mesophilic microorganisms, growth is usually inhibited at low phenol concentrations, requiring low level feeding or slow release "phenol sinks" for successful utilization. This enzyme has been shown to be substrate inhibited above 0.3 mM phenol concentration both in *Pseudomonas putida* and *Trichosporon* yeast.

It is recognized that thermostable enzymes are frequently also more resistant to chemical denaturation. This suggests that if suitable pathways exist, biotransformation of environmental pollutants might be possible at concentrations toxic to mesophiles. Although little is known about aromatic pathways in thermophiles, Buswell, J. A., and D. G. Twomey, J. Gen. Microbiol. 87:377–379 (1975)) and Buswell, J. A., Biochem. and Biophysical Res. Comm. 60:934–941 (1974) isolated a strain of *B. stearothermophilus* capable of phenol degradation which utilized an NADH dependent phenol hydroxylase. This strain was inhibited by phenol concentrations above 5 mM, and phenol inhibition of the phenol hydroxylase was not studied.

U.S. Pat. Nos. 3,700,560 to Oppermann and 4,508,822 to Taylor describe the preparation of cyclic dihydroxy compounds from aromatic compounds using enzymes or bacteria. In general, the degradative pathway for the dicyclic dihydroxyl compounds is not present.

Pyrocatechol is an intermediate in the pathway for the degradation of phenol which is generally modified to a significant extent as it is formed. Because of its wide utilization in the plastic and photographic industries, efficient bioproduction of pyrocatechol could provide an alternative to chemical production processes if it could be achieved. Other cyclic hydroxides are also useful.

OBJECTS

It is therefore an object of the present invention to provide a method which allows bacterial production of a cyclic hydroxide from a compound having a benzene ring. Further, it is an object of the present invention to provide improved bacterial strains for such bioconversion. Further still, it is an object of the present invention to provide a method which is simple and economical. These and other objects will become increasingly apparent by reference to the following description and the drawings.

IN THE DRAWINGS

FIG. 1A and 1B show growth kinetics and phenol degradation by *Bacillus stearothermophilus* BR219. FIG. 1A shows growth and FIG. 1B shows phenol degradation at concentrations of: 0 mM; 5mM; 10 mM; 15 mM; 20 mM. The symbols correspond in FIGS. 1A and 1B.

FIG. 2 shows the temperature dependence of the activity of the extracted phenol hydroxylase.

FIGS. 3A and 3B show phenol and NADH substrate affinities of the extracted phenol hydroxylase. FIG. 3A shows NADH varied and 100 $\mu$M phenol. FIG. 3B shows phenol varied and 1 mM NADH.

GENERAL DESCRIPTION

Figure 1A:
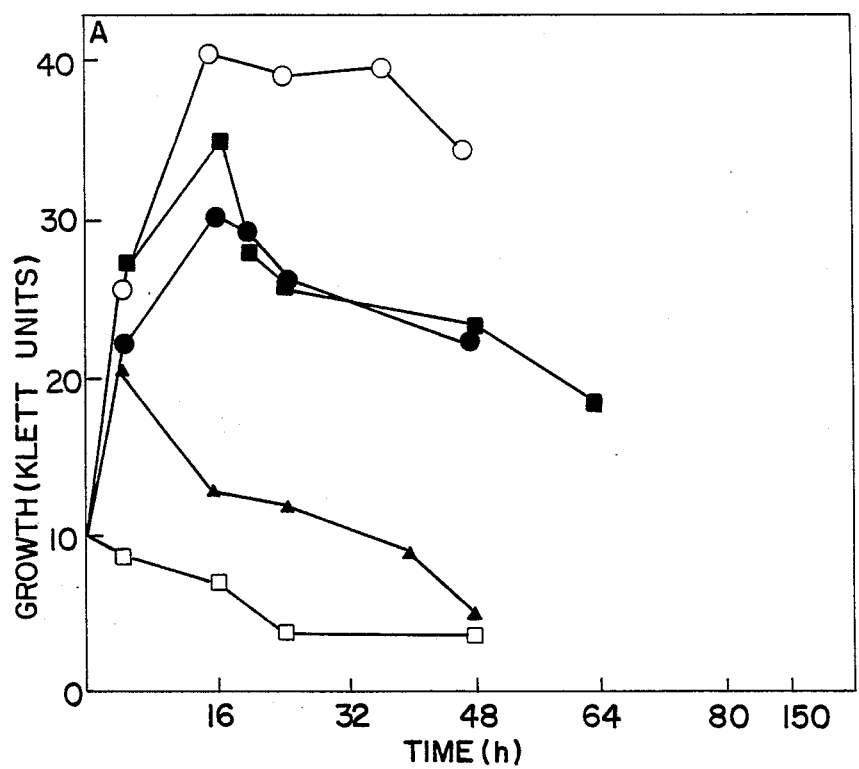

The present invention relates to a process for producing a cyclic hydroxide from a compound having a benzene ring which comprises: providing a Bacillus which metabolizes phenol in a growth medium with the compound having the benzene ring and an effective amount of tetracycline which inhibits degradation of the cyclic hydroxide by the Bacillus; and modifying the compound having the benzene ring with the Bacillus to produce the cyclic hydroxide.

The present invention particularly relates to a process for producing pyrocatechol from phenol which comprises: providing a Bacillus which metabolizes phenol in a growth medium with the phenol and an effective amount of tetracycline which inhibits degradation of the pyrocatechol by the Bacillus; and modifying the phenol with the Bacillus to produce pyrocatechol.

Thus the process of the present invention can be used to convert aniline to o-hydroxyl aniline. Further aromatic monohydroxides can be converted to aromatic or cyclic dihydroxides. Numerous such compounds containing a benzene ring are well known to those skilled in the art as shown by Buswell et al, J. Gen Microbiology 87:377-379 (1975).

Further, the present invention relates to a preferred biologically pure culture of *Bacillus stearothermophilus* ATCC 67824. Further still, the present invention relates to a biologically pure culture of *Bacillus stearothermophilus* containing transposon Tn916 integrated with DNA of *Bacillus stearothermophilus* ATCC 67824 and exhibiting enhanced resistance to tetracycline due to the transposon Tn916.

The preferred culture is deposited under the Budapest Treaty in the American Type Culture Collection as ATCC 67824. The culture is referred to in the following description as *Bacillus stearothermophilus* BR219. It will be appreciated that other Bacillus which metabolize phenol and which are resistant to phenol can be used; however, strain BR219 is preferred. Bacilli which are thermophilles providing growth on phenol at (temperatures 40° to 80° C.) are most preferred.

BR219 can also contain transposon Tn916 which encodes for tetracycline resistance as discussed hereinafter. However, the transposon need not be present in BR219 in order to perform the described process.

Preferably the tetracycline and compound to be treated are added at the end of the exponential phase of growth of the Bacillus. The production of the pyrocatechol is over a period of 1 to 24 hours. The amount of tetracycline is preferably between 1 and 20 micrograms per ml of the growth media. The amount of phenol or other compound is between about 5 and 20 mM in the growth media, preferably about 10 mM for BR219.

SPECIFIC DESCRIPTION

Example 1 describes the isolation of phenol tolerant strain of *B. stearothermophilus* BR219 and the solubilization and initial characterization of its phenol hyroxylase which is resistant to both heat and phenol.

EXAMPLE 1

MATERIALS AND METHODS

Biological materials and conditions: Bacterial strains used are listed in Table 1.

TABLE 1

Thermophilic Bacilli tested for phenol metabolism

| Strain | Characteristics | Phenol utilization | Source |
|---|---|---|---|
| *Bacillus stearothermophilus* | | | |
| BR 132 | prototroph, parent strain | +* | ATCC 31195 |
| BR 133 | prototroph | − | ATCC 57953 |
| BR 134 | prototroph | − | ATCC 12980 |
| BR 135 | prototroph | − | ATCC 29609 |
| BR 230 | β-galactase constitutive | − | Hannah Research Inst. Scotland |
| BR 231 | β-galactase constitutive | − | Hannah Research Inst. Scotland |
| BR 219 | phenol+, amylase− | ++* | ATCC 67824 |
| *Bacillus caldolyticus* | | | |
| BL 116 | spc$^r$, cd$^r$ | − | Derivative of NRL1623 |
| BL 247 | spc$^r$, cd$^s$ | − | SDS curing of BL 116 |

*Yellow color formation upon addition of pyrocatechol.
spc$^r$—spectinomycin resistant
cd$^r$—cadmium resistant
cd$^s$—cadmium sensitive

*B. stearothermophilus* BR219 was isolated from the Tittabawassee River sediment, near Midland, Mich. which is known to be contaminated with phenol. To isolate this bacterium, 1 g (dry weight) sample of a sediment was suspended in 1/100th concentration of L broth containing 5 mM phenol and incubated at 55° C. After 2 days, a small amount of inoculum was transferred to 100 ml basal medium ($K_2HOP_4$ 0.5 g; $NH_4Cl$ 1.0 g; $MgSO_4.7H_2O$ 20 mg; yeast extract 0.2 g; casamino acids 0.1 g and 1 ml trace element solution per liter as described in Buswell, J. A., J. Bacteriol. 124:1077–1083 (1975), containing 5 mM phenol., incubated with shaking for 3 days at 55° C. Serial dilutions were plated on basal medium containing 5 mM phenol and 15 g of Bacto-agar (Difco Laboratories, Detroit, Mich.) per liter. Isolated colonies were selected and successively streaked onto these plates. For liquid culture, strain BR219 was grown to the early stationary phase in the basal medium containing 5 mM phenol. The cultures were then diluted at least 100-fold with basal medium to obtain the initial cell densities used in the experiments. The identification tests for BR219 were carried out according to standard as set forth in Bergy's Manual of Determinative Bacteriology, 8th ed., Williams and Wilkins, Baltimore (1974)). Screening of *B. stearothermophilus* strains for phenol utilization: Strains of *B. stearothermophilus* were tested on basal plates containing 5 mM phenol. After 24 h of growth, the colonies that appeared were sprayed with pyrocatechol (1 mg/ml) to test for yellow 2-hydroxymuconic semialdehyde formation. Determination of growth and phenol degradation: Basal medium, 40 ml in 300 ml Erlenmeyer flasks were amended with filter sterilized phenol to a final concentration of 5, 10, 15 and 20 mM. One ml of 8 h phenol-grown culture was inoculated ($4 \times 10^6$ cells) into each flask and incubated at 55° C. with shaking. Aliquots of the cultures were removed at intervals and growth was monitored in Klett and Summerson colorimeter. Residual phenol was determined according to Martin (Martin, R. W., Anal. Biochem. 21:1419–1420 (1949)).

Analysis of phenol metabolites: Phenol-grown cultures were sampled at intervals, centrifuged at 6,000×g for 15 minutes and the supernatant was adjusted to pH 2.0 with 1 N HCl and extracted with either ethyl acetate or diethyl ether. The organic extracts were treated with anhydrous sodium sulfate to remove water and then evaporated to dryness. The residue was dissolved in methanol. Qualitative analysis of the phenol metabolite was carried out in thin layer chromatograms (Silica gel 60 F 254+366, 20×20 cm, thickness 2 mm, Merck, West Germany) and developed in benzene:dioxane:acetic acid (60:36:4 v/v) as well as on benzene:ethanol (10:1 v/v). The dried plates were examined under UV light and were sprayed with a mixture of equal parts of 0.3% solutions of ferric chloride and potassium ferricyanide. Duplicate plates were sprayed with catechol reagent of Irie et al (Irie, S., K. Shirai, S. Doi, and T. Yorifuji, Agric. Biol. Chem. 51:1489–1493 (1987)). For analysis of pyrocatechol, an aliquot of a culture supernatant was withdrawn and made up to 1 ml with sterile distilled water, mixed with 1 ml of a solution containing 0.1% 4-aminoantipyrine, 2% sodium carbonate and 0.02 N NaOH. The absorbence was read at 515 nm after 20 minutes (Irie, S., K. Shirai, S. Doi, and T. Yorifuji, Agric. Biol. Chem. 51:1489–1493 (1987)).

Preparation of cell extract: All steps of the preparation were carried out at 4° C. Exponential phase culture in 2 l quantity was harvested and washed with 0.1 M phosphate buffer, pH 7.6 by centrifugation at 6,000×g for 15 minutes. The pellet was suspended in 20 ml of the same buffer and disrupted for 2 minutes with 10 second intervals using a Cole Parmer 4710 ultrasonic homogenizer. The homogenized suspension was centrifuged at 26,890×g for 20 minutes (Sorvall RC2). The resultant supernatant served as crude enzyme source. The enzyme activity was stable at −20° C. for several days.

Phenol hydroxylase (EC.1.14.13.7): Attempts to demonstrate phenol hydroxylase in BR219 cell extracts using oxidation of NADPH or NADH, or oxygen uptake studies (Neujahr, H. Y., and A. Gaal, Eur. J. Biochem. 35:386–400 (1973)), showed enzyme activity which was only partially dependent on phenol. Therefore, an assay system was implemented which measured phenol disappearance directly.

Enzyme activity was determined by using 1 ml of a reaction mixture which was 100 µM phenol, 1 mM NADH and 100 mM phosphate buffer (pH 7.6). One ml assay mixture with enzyme was incubated for 15 minutes at 55° C. and stopped by the addition of 12 µl of 2% 4-aminoantipyrine followed by 40 µl 2 N ammonium hydroxide and 40 µl of 2% potassium ferricyanide. The final volume was made up to 2 ml with distilled water. Following incubation at room temperature for 20 minutes, absorbence was read at 510 nm. Standards were prepared for each assay and the absorbence was linear up to 100 µM phenol. The activity unit is defined as µM of phenol used per minute. Controls included omission of enzyme, omission of NADH, and 0 time reactions.

Chemicals: NADH, NADPH, and FAD, were purchased from Sigma Chemical Co., (St. Louis, Mo.).

Phenol utilization by *B. stearothermophilus*: In order to determine the generality of phenol utilization, a group of *B. stearothermophilus* and representative *B. caldolyticus* strains were tested for phenol utilization using growth on minimal plates containing 5 mM phenol (Table 1). Of the group, only weak growth was shown by BR132, indicating that phenol utilization was not a common characteristic. BR132 was also the only strain that showed yellow color formation upon addition of pyrocatechol.

Characterization of the isolate: Of the series of isolates obtained using phenol enrichment, only strain BR219 exhibited strong growth on minimal plates containing phenol, showed limited growth on the same plates in the absence of phenol, and yellow color appearance upon addition of pyrocatechol to the phenol-grown colonies. Moreover, the BR219 colonies grown on minimal plates in the absence of phenol did not develop yellow color upon addition of pyrocatechol. This isolate was characterized as shown in Table 2.

TABLE 2

| Comparison of *B. stearothermophilus* BR 219 with BR 135 | | |
|---|---|---|
| Characteristic | BR 219 | BR 135 |
| Shape | rod | rod |
| Gram stain | + | + |
| Nitrate reduction to nitrite | W | + |
| Catalase | + | + |
| Oxidase | + | − |
| Hydrolysis of gelatin | + | + |
| Hydrolysis of starch | − | + |
| Hydrolysis of casein | + | + |
| Indole formation | − | − |
| Citrate utilization | − | − |
| Sodium azide utilization | − | − |
| Anaerobic growth | − | − |
| Growth in the presence of 3% (W/V) NaCl | + | + |
| Growth in the presence of 5% (W/V) NaCl | − | − |
| Maximum growth temperature | 75° C. | 70° C. |
| Sensitivity to antibiotics | | |
| Ampicillin | s | s |
| Chloramphenicol | s | s |
| Kanamycin | s | s |
| Tetracycline | sl | s |
| Spore stain | green | green |
| Spore shape | swollen, | swollen, |

TABLE 2-continued

| Comparison of *B. stearothermophilus* BR 219 with BR 135 | | |
|---|---|---|
| Characteristic | BR 219 | BR 135 |
| | terminal | terminal |

+ positive
− negative
W Weakly positive
s sensitive
sl stop the cells from growing Except for absence of amylase and oxidase activities, the characteristics resemble those described for *B. stearothermophilus* as exemplified by BR135 (ATCC 29609). Thus BR219 is designated as a strain of *B. stearothermophilus*, which resembles PH 24 in its absence of amylase activity (Buswell, J. A., and D. G. Twomey, J. Gen. Microbiol. 87:377–379 (1975)).

Figure 1B:
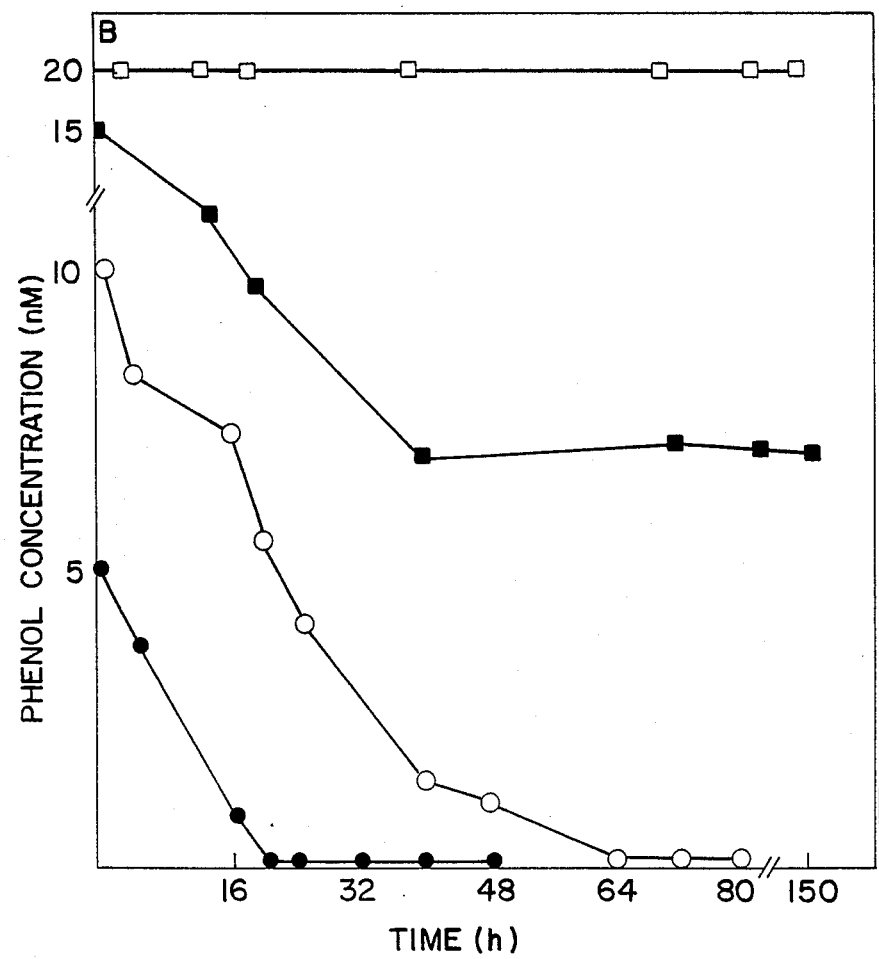

Growth studies of BR219 on phenol showed that this strain could grow on phenol at levels to 15 mM, with 10 mM giving optimal growth (FIG. 1A). In 10 mM phenol, the generation time was 101 minutes. Phenol measurements during growth indicated that at initial levels of 5 and 10 mM, complete disappearance of phenol was observed, while at 15 mM, only 50% of phenol was degraded at 160 h (FIG. 1B). Growth on phenol at levels to 15 mM indicates that the isolate withstands and degrades higher levels than those reported for pseudomonads.

Figure 2:
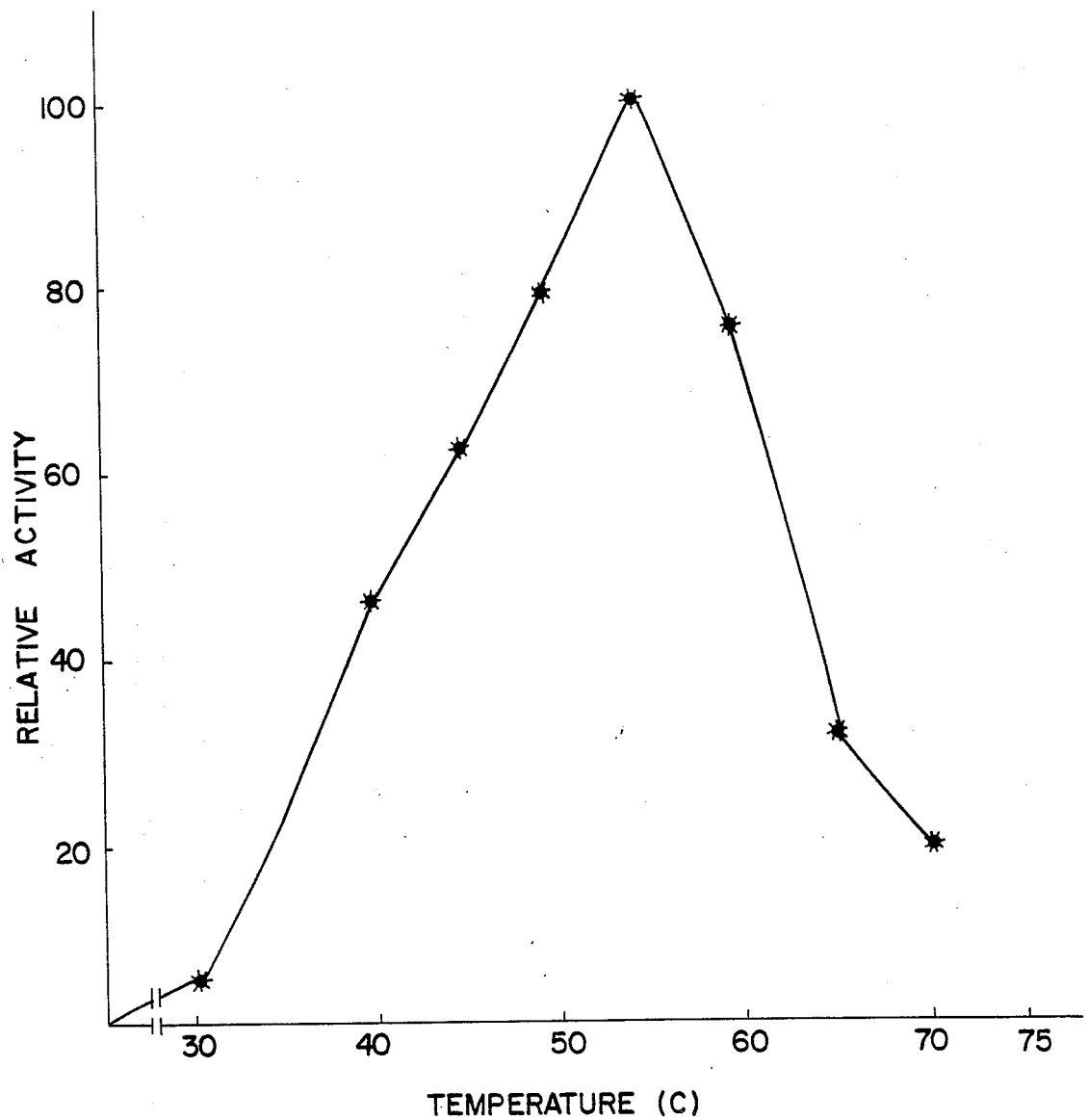
Figure 3A:
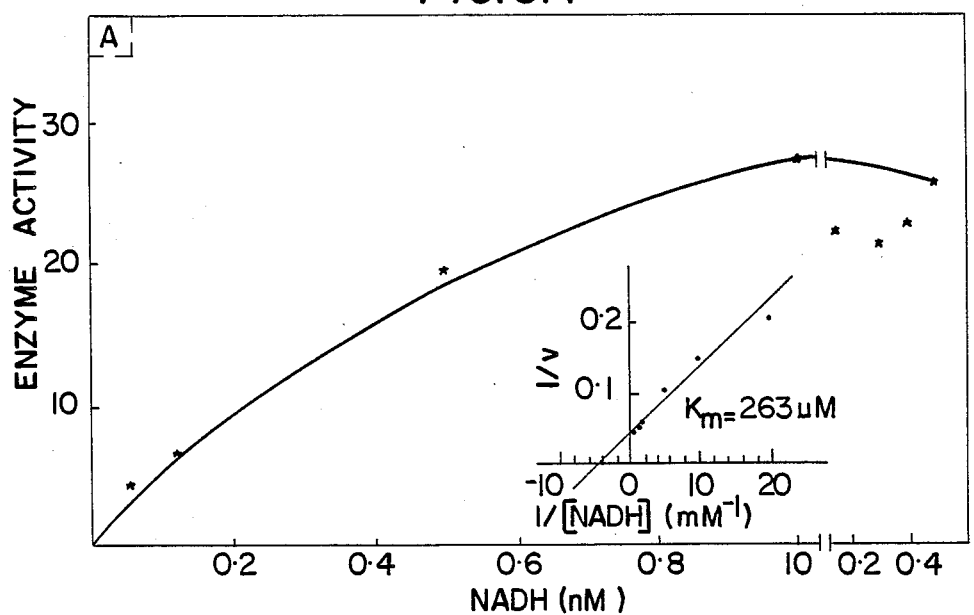
Figure 3B:
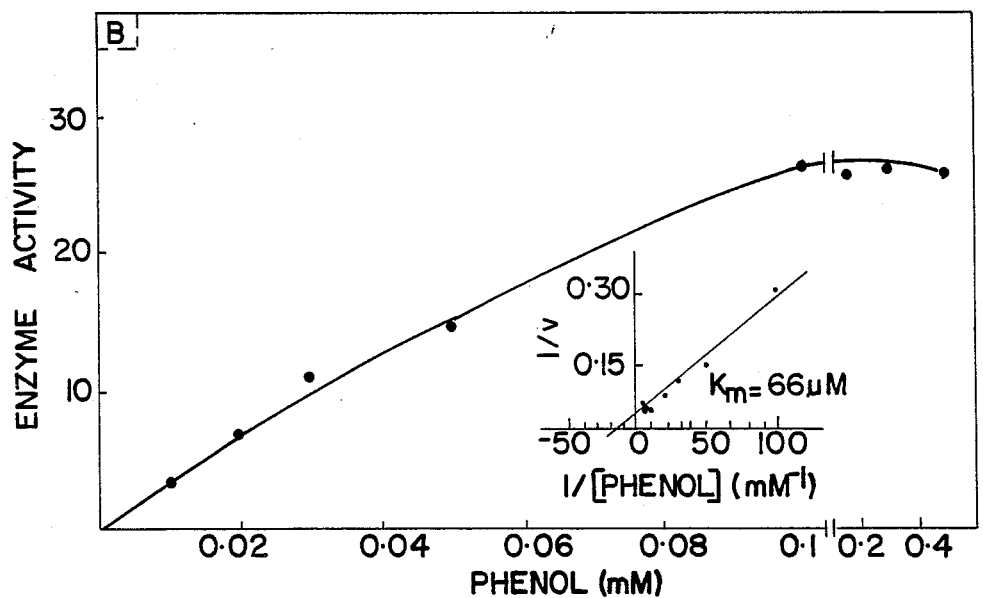

Properties of phenol hydroxylase: Phenol hydroxylase activity in solubilized extracts was linear with both time and protein concentration, and unaffected by NADPH and FAD addition. Maximum activity at 55° C. was measured, verifying the anticipated thermostability of the enzyme (FIG. 2). Phenol hydroxylase activity increased with increasing concentrations of phenol to 0.1 mM, and did not show substrate inhibition even up to 0.5 mM phenol, the highest level tested (FIG. 3). Km values for phenol and NADH were 66 µM and 263 µM, respectively. Inhibitors of the phenol hydroxylase activity are shown in Table 3.

TABLE 3

| Effect of inhibitors on phenol hydroxylase | | |
|---|---|---|
| Inhibitors (0.1 mM) | Enzyme activity[a] | Percent Inhibition |
| Copper sulfate | 2.3 | 91 |
| Ferrous sulfate | 15.1 | 43 |
| Mercuric chloride | 3.4 | 87 |
| Sodium chloride | 13.7 | 48 |
| o-Phenanthroline | 0 | 100 |
| p-Chloromercuribenzoate | 3.5 | 87 |
| Ethylene diaminetetraacetic acid | 6.0 | 77 |
| Diethyldithiocarbamate | 26.4 | 0 |
| None | 26.4 | 0 |

[a]Enzyme activity was measured in 1 ml of reaction mixture containing 0.1 M phosphate buffer, pH 7.6; NADH, 1 mM; phenol, 100 µM and enzyme (140 µg).

Catechol 2,3-dioxygenase was also observed in cell extracts at a level of 21.3 U/mg protein, but has not yet been characterized. No phenol hydroxylase or catechol 2,3-dioxygenase as observed in cell extracts of BR219 grown on sodium succinate (2%) rather than phenol, indicating that this meta degradation pathway is induced by phenol.

The phenol tolerance of BR219 and lack of phenol substrate inhibition of BR219 phenol hydroxylase significantly differs from properties observed with mesophiles.

EXAMPLE 2

This Example 2 describes the use of tetracycline to inhibit the phenol metabolism of BR219 so as to accumulate pyrocatechol.

METHODS AND MATERIALS

Measurement of Pyrocatechol

Pyrocatechol was measured colorimetrically using the 4-aminoantipyrene method of Irie et al (Irie, S., K. Shirai, S. Doi, and T. Yorifuji, Agric. Biol. Chem. 51:1489–1493 (1987)). Independent identification of pyrocatechol was made using thin layer chromatography.

Organism and Media

BR219 was isolated as in Example 1. It was grown on DP medium of Buswell (Buswell, J. A., J. Bacteriol. 124:1077–1083 (1975)) containing phenol at the concentration indicated hereinafter. Growth was measured using apparent optical density at 515 nm on a Cary 15 spectrophotometer, or by viable count of suitable dilutions on L agar plates. BR219 transconjugants containing the conjugating transposon Tn916, were isolated at 55° C. on L agar plates with 5 µg/ml tetracycline following 48° C. liquid culture mating with *Bacillus subtilis* BS114 containing the transposon integrated in the chromosome.

Intracellular 2-Hydroxymuconic Semialdehyde

The relative activity of catechol 2,3 dioxygenase was measured using the appearance of 2-hydroxymuconic semialdehyde following addition of known amounts of pyrocatechol to the culture. For this, pyrocatechol was added to 100 µgm/ml to log phase cells which had been grown in the medium of Buswell, cited previously, containing 10 mM phenol nd resuspended in the medium with no phenol to OD 0.5 at 515 nm in a Cary ™ 15 spectrophotometer. The reference beam contained the same cell concentration with no pyrocatechol addition. Formation of 2-hydroxymuconic semialdehyde was observed by the appearance of an absorption band at 375 nm, which was recorded 15 minutes after catechol addition.

Assay of 2,3 Catechol Dioxygenase

Cellular extracts of BR219 were made of log phase cells using the method of Buswell, cited previously.

Initial experiments indicated that although small amounts of catechol were formed in overnight flask cultures growing on phenol, significant enhancement of pyrocatechol accumulation with the addition of tetracycline to the culture at the end of the exponential growth phase as shown in Table 4.

TABLE 4

| Catechol production (µgm/ml) by B. stearothermophilus BR219 | | |
|---|---|---|
| | No tetracycline | 5 mM tetracycline |
| BR219 | 2.2 | 7.2 |
| BR219::Tn916 | 1.2 | 12.8 |

Tetracycline was added in late exponential phase, and pyrocatechol measured 16 hours thereafter.

Figure 4:
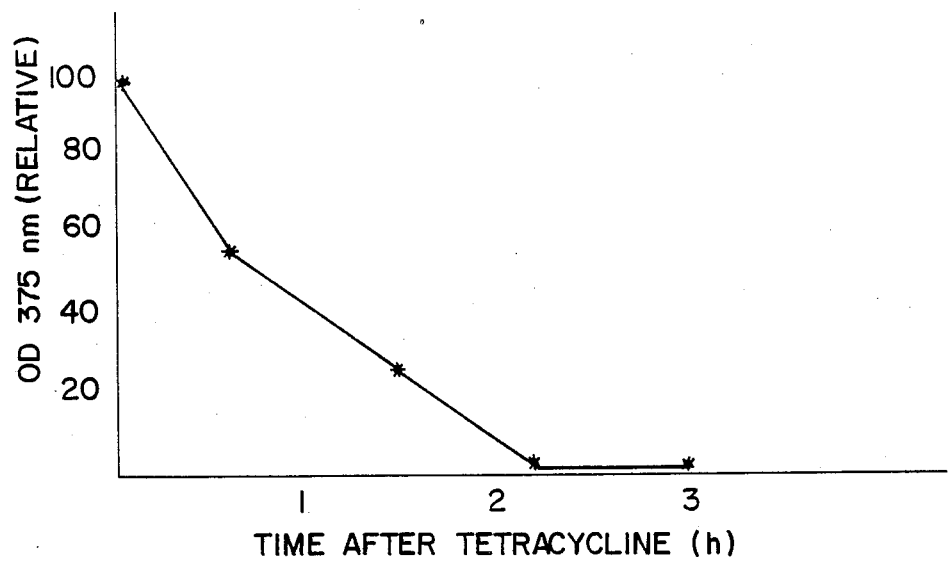
FIG. 4 shows the reduction of 2-hydroxymuconic semialdehyde production from pyrocatechol as a result of tetracycline addition to the growth medium.

Accumulation of pyrocatechol with addition of tetracycline suggested that tetracycline might act through direct inhibition of catechol 2,3 dioxygenase. This inactivation was measured through addition of pyrocatechol to resuspended cultures and measurement of intracellular 2-hydroxymuconic semialdehyde. As seen in FIG. 4A, cellular accumulation of 2-hydroxymuconic semialdehyde following pyrocatechol addition was lost rapidly after tetracycline treatment with no activity evident after 2 hours. During this period, there was no loss in cell viability. Verification of direct catechol 2,3 dioxygenase inhibition by tetracycline was carried out using crude cell extracts, where complete inhibition of catechol 2,3 dioxygenase activity as observed at tetracycline concentrations above 1 µgm/ml.

Figure 5:
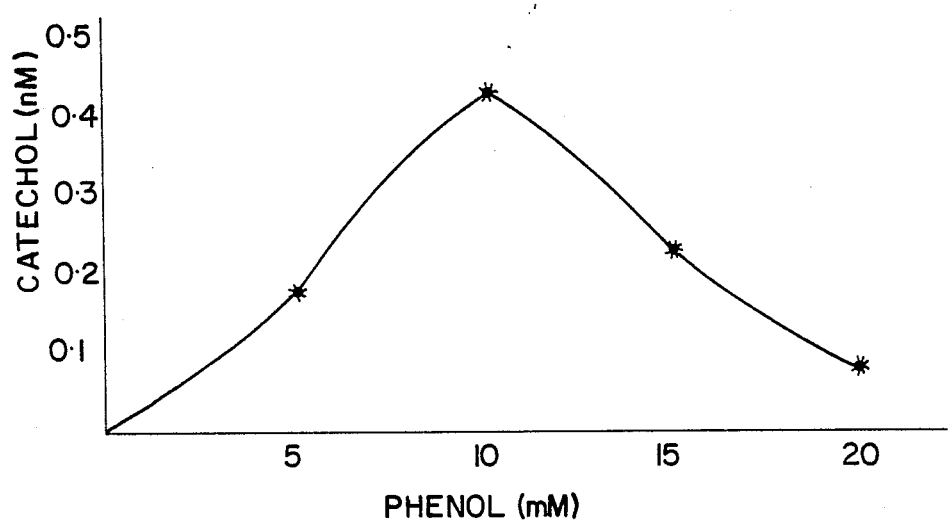
FIG. 5 shows pyrocatechol production in the presence of tetracycline at various phenol concentrations.

It was of interest to determine the optimal concentration of phenol that could be used for pyrocatechol production. As seen in FIG. 5, 10 mM phenol proved to be the optimum concentration for pyrocatechol formation in this system.

Bioaccumulation of the metabolic intermediate pyrocatechol can be achieved through addition of tetracycline in the cells of *Bacillus stearothermophilu* in culture, which inhibits catechol 2,3 dioxygenase in cell extracts and blocks intracellular oxidation of pyrocatechol to 2-hydroxymuconic semialdehyde. Introduction of transposon Tn916 further aids pyrocatechol production, possibly by countering antibiotic inhibition of protein synthesis.

It is intended that the foregoing description be only illustrative of the present invention and that the present invention be limited only by the hereinafter appended claims.

We claim:

1. A process for producing a cyclic hydroxide from a compound having a benzene ring which comprises:
    (a) providing a *Bacillus stearothermophilus* which metabolizes phenol in a growth medium containing between about 5 mM and 20 mM of phenol with the compound having the benzene ring and an effective amount of tetracycline which inhibits degradation of the cyclic hydroxide by the *Bacillus stearothermophilus*; and
    (b) modifying the compound having the benzene ring with the Bacillus to produce the cyclic hydroxide.

2. The process of claim 1 wherein the tetracycline concentration is between about 1 and 20 µgm/ml.

3. The process of claim 1 wherein the *Bacillus stearothermophilus* is obtained by mating a tetracycline sensitive *Bacillus Stearothermophilus* with a parent bacterium which contains transposon Tn916 encoding for tetracycline resistance and then isolating the *Bacillus stearothermophilus* which is tetracycline resistant.

4. The process of claim 3 wherein the parent bacterium is *Bacillus subtilis*.

5. The process of claim 1 wherein the tetracycline is added to the growth medium at the end of the exponential phase of growth of the *Bacillus stearothermophilus*.

6. A process for producing pyrocatechol from phenol which comprises:
    (a) providing a *Bacillus stearothermophilus* which metabolizes phenol in a growth medium containing between about 5 and 20 mM with the phenol and an effective amount of tetracycline which inhibits degradation of the pyrocatechol by the *Bacillus stearothermophilus*; and
    (b) modifying the phenol with the Bacillus to produce pyrocatechol.

7. The process of claim 6 wherein the phenol is at a concentration between about 5 and 20 1 mM in the growth medium.

8. The process of claim 6 wherein the tetracycline concentration is between about 1 and 20 μgm/ml.

9. The process of claim 6 wherein the *Bacillus stearothermophilus* is obtained by mating a tetracycline sensitive *Bacillus stearothermophilus* with a parent bacterium which contains Transposon Tn916 encoding for tetracycline resistance and then isolating the *Bacillus stearothermophilus* which is tetracycline resistant.

10. The process of claim 9 wherein the parent bacterium is *Bacillus subtilis*.

11. The process of claim 6 wherein the tetracycline is added to the growth medium at the end of the exponential phase of growth of the *Bacillus stearothermophilus*.

12. The process of claim 11 wherein the modifying is for between about 1 and 24 hours.

13. The process of claim 6 wherein the *Bacillus stearothermophilus* contains transposon Tn916 integrated with DNA of the *Bacillus stearothermophilus*.

14. The process of claim 6 wherein the Bacillus is *Bacillus stearothermophilus* ATCC 67824.

15. The process of claim 6 wherein the tetracycline is at a concentration between about 1 and 20 gm/ml, and wherein the tetracycline is added to the growth medium at the end of the exponential phase of growth of the Bacillus.

16. The process of claim 15 wherein the modifying is for between about 1 and 24 hours.

17. The process of claim 16 wherein the *Bacillus stearothermophilus* contains transposon Tn916 integrated with DNA of the *Bacillus stearothermophilus*.

18. The process of claim 16 wherein the *Bacillus stearothermophilus* is *Bacillus stearothermophilus* ATCC 67824.

* * * * *